US007225554B2

(12) United States Patent
Madsen (10) Patent No.: US 7,225,554 B2
(45) Date of Patent: Jun. 5, 2007

(54) APPARATUS AND METHOD FOR MEASURING A HUMAN HEAD

(75) Inventor: Joseph R. Madsen, Newton, MA (US)

(73) Assignee: Children's Hospital Boston, Boston, MA (US)

( * ) Notice: Subject to any disclaimer, the term of this patent is extended or adjusted under 35 U.S.C. 154(b) by 0 days.

(21) Appl. No.: 11/069,805

(22) Filed: Feb. 28, 2005

(65) Prior Publication Data
US 2005/0223580 A1 Oct. 13, 2005

Related U.S. Application Data

(60) Provisional application No. 60/548,641, filed on Feb. 27, 2004.

(51) Int. Cl.
*A61B 5/103* (2006.01)
*G01B 5/20* (2006.01)

(52) U.S. Cl. .............. 33/512; 33/552; 600/587

(58) Field of Classification Search ............... 33/2 R, 33/512, 514.1, 514.2, 546, 550, 551, 552, 33/555.1, 561.1, 561.2, 561.3; 600/587
See application file for complete search history.

(56) References Cited

U.S. PATENT DOCUMENTS

| | | | |
|---|---|---|---|
| 37,759 A | 2/1863 | Klein | |
| 144,855 A | 11/1873 | McKnight | |
| 268,614 A | 12/1882 | Brown | |
| 390,178 A | 9/1888 | Lyons | |
| 470,912 A | 3/1892 | Durand | |
| 1,322,395 A | 11/1919 | Baker | |
| 1,469,640 A | 10/1923 | Graff | |
| 1,897,941 A | 2/1933 | Lavery | |
| 2,081,133 A * | 5/1937 | Bisel | 33/2 R |
| 2,295,447 A * | 9/1942 | Bierman | 33/514.2 |
| 2,394,489 A | 2/1946 | Rowe | |
| 3,945,122 A | 3/1976 | Durand et al. | |
| 4,875,488 A * | 10/1989 | Shimazu et al. | 600/587 |
| 5,014,440 A * | 5/1991 | Lessi et al. | 33/552 |
| 5,911,126 A | 6/1999 | Massen | |
| 5,926,388 A | 7/1999 | Kimbrough et al. | |
| 6,026,351 A * | 2/2000 | Takeuchi | 33/503 |
| 6,340,353 B1 | 1/2002 | Pomatto et al. | |
| 6,438,859 B1 | 8/2002 | Lynch | |
| 6,527,711 B1 | 3/2003 | Stivoric et al. | |
| 6,572,572 B2 | 6/2003 | Pomatto et al. | |
| 2005/0166414 A1* | 8/2005 | Lum et al. | 33/550 |
| 2006/0075648 A1* | 4/2006 | Madsen et al. | 33/512 |

OTHER PUBLICATIONS

Reyes Enciso, "3D head anthropometric analysis".
Letter to the Editor, "Orthotic Versus Nonorthotic Treatment for Occipital Plagiocephaly" 6 pages.
Glossary.

* cited by examiner

*Primary Examiner*—G. Bradley Bennett
(74) *Attorney, Agent, or Firm*—Joel E. Lutzker, Esq.; Jason Marin, Esq.; Schulte Roth & Zabel (57) ABSTRACT

The invention relates to apparatus and methods for measuring a human head. The apparatus disclosed herein involve the use of linear rulers, or rotating contacting members, coupled to a support member. The apparatus disclosed herein can be positioned on a human head, using the methods disclosed herein, to determine the outer contour of the head. Such a measurement can aid in the diagnosis and monitoring of various abnormalities of the human head, including plagiocephaly.

20 Claims, 6 Drawing Sheets

APPARATUS AND METHOD FOR MEASURING A HUMAN HEAD

1. BACKGROUND

A need exists for a cost efficient method to measure and follow the shape of the heads of infants. Measuring head or cranial shape has been a mainstay in the treatment of cranial synostosis for decades, but with the increasing prevalence of positional plagiocephaly it has become a major reason for referral to neurosurgical clinics by pediatricians and by parents. Conditions of the head such as sagittal synostosis resulting in a long and narrow head, can be suspected or even diagnosed on the basis of cranial measurements, as can the situations of flattening of the back or asymmetrical flattening of the head related to the position in which a baby sleeps. Orthotic devices are often used to treat the conditions which do not actually require surgery, and the ability to make inexpensive and repeated measurements would be useful in evaluating the need for treatment of a particular patient as well as the response to treatment of any individual patient, and the effectiveness of any particular therapeutic intervention.

Traditionally, measurements of cranial shape have been made either on radiographs which require radiation exposure, or with the use of large calipers which require the points of the calipers to be placed at particular locations on a infant's head. This introduces significant operator dependency on the accuracy of the measurement, and purchase of the calipers has limited their use generally to highly-skilled neurosurgeons and others who see a large number of these cases.

Furthermore, diagnosis of cranial abnormalities and/or diseases are often made on physical exam by clinicians without quantifying the shape of the outer contour of the subject's head. This makes it difficult for the clinician to accurately diagnose a cranial disease and/or abnormality and makes it difficult for the clinician and/or parents to track the progression or regression of a particular subject's cranial disease and/or abnormality.

2. SUMMARY OF THE INVENTION

One aspect of the invention is an apparatus for measuring an outer contour of a human head, comprising a support member and a plurality of contacting members for contacting a human head.

In a particular embodiment of the invention, at least one of the contacting members is pivotally mounted on the support member. In a further embodiment, the contacting members are adjustable. In another embodiment of the invention, the apparatus comprises at least one radially adjustable contacting member. In one embodiment of the invention, the apparatus comprises at least 1 adjustable contacting member. In another embodiment of the invention, the apparatus comprises at least 2, 3, 4, 5, 6, 7, 8, 9, 10, 11, 12, 13, 14, 15, 16, 17, 18, 19 or 20 adjustable contacting members. In yet another embodiment, the apparatus comprises at least one fixed contacting member. In a further embodiment of the invention, the apparatus comprises at least 2, 3, 4, 5, 6, 7, 8, 9, 10, 11, 12, 13, 14, 15, 16, 17, 18, 19 or 20 fixed contacting members. Another embodiment of the invention encompasses an apparatus that comprises at least one adjustable contacting member and at least one fixed contacting member. In another embodiment of the invention, at least one of the contacting members is rotatably mounted on the support member. In another embodiment, the apparatus comprises a sensor. In a further embodiment, the apparatus comprises a transmitter. In a specific embodiment, the transmitter is a wireless transmitter. In yet another embodiment the apparatus comprises at least one contacting member. In a further embodiment, the apparatus comprises at least 4 contacting members. In yet another embodiment, the apparatus comprises at least 12 contacting members. In another embodiment, the apparatus comprises at least 2, 4, 5, 6, 7, 8, 9, 10, 11, 13, 14, 15, 16, 17, 18, 19 or 20 contacting members. In yet another embodiment of the invention, at least two of the contacting members are connected to each other so that an adjustment to one of the connected contacting members causes an adjustment to the at least one other connected contacting member. In another embodiment the contacting member is for contacting a portion of a human ear, including but not limited to the external auditory meatus. Such a contacting member comprises a portion that conforms to an external auditory meatus of a human head.

In one embodiment of the invention, the apparatus comprises a support member and a plurality of contacting members rotatably coupled to the support member wherein each of the plurality of contacting members comprises a curved surface for contacting with the human head and wherein the curved surface of each contact member has a radius of curvature that is one of increasing and decreasing in a direction of rotation. In a specific embodiment, the curved surface of the contacting member comprises a portion which is characterizable by a spiral equation. In a further embodiment, the spiral equation characterizes a linear spiral. In another embodiment the spiral equation characterizes a logarithmic spiral. In another embodiment, the apparatus comprises a support member and a plurality of contacting members wherein at least two contacting members are rotatably coupled to the support member at the same coupling point. In another embodiment, the apparatus comprises a support member and a plurality of contacting members wherein at least two contacting members are rotatably coupled to the support member at the same coupling point.

In another embodiment of the invention, the apparatus comprises a support member and a plurality of adjustable contacting members coupled to the support member, wherein each of the plurality of adjustable contacting members comprises a surface for contacting with the human head, at least one of the adjustable contacting members comprises a mechanism for locking the adjustable contacting member. In a further embodiment, at least two of the adjustable contacting members are connected to each other so that an adjustment to one of the connected adjustable contacting members causes an adjustment to the at least one other connected adjustable contacting member.

In another embodiment of the invention, the apparatus comprises a support member and a plurality of adjustable contacting members coupled to the support member, wherein each of the plurality of adjustable contacting members comprises a surface for contacting with the human head, the support member comprises a mechanism for locking at least one of the adjustable contacting members. In a specific embodiment, at least two of the adjustable contacting members are connected to each other so that an adjustment to one of the connected adjustable contacting members causes an adjustment to the at least one other connected adjustable contacting member.

In another embodiment, the apparatus comprises a locking mechanism. In a further embodiment, the support member and/or the contacting members comprise a locking mechanism.

In yet another embodiment of the invention, the apparatus comprises a support member and a plurality of radially adjustable contacting members coupled to the support member, wherein a contact surface of the radially adjustable contacting members to be contacted with the human head moves radially. In a further embodiment, at least two of the radially adjustable contacting members are connected to each other so that an adjustment to one of the radially adjustable contacting members causes an adjustment to the at least one other connected radially adjustable contacting member.

In another embodiment of the invention, the apparatus comprises a support member and at least four adjustable contacting members coupled to the support member, wherein each of the at least four adjustable contacting members comprises a surface for contacting with the human head and the adjustable contacting members have indicia thereon for determining the outer contour of a human head. In a specific embodiment, the contacting members are radially adjustable.

In another embodiment of the invention, the apparatus comprises a support member and at least four adjustable contacting members coupled to the support member, wherein each of the at least four adjustable contacting members comprises a surface for contacting with the human head and the support member has indicia thereon for determining the outer contour of a human head. In a specific embodiment, the contacting members are radially adjustable.

In another embodiment of the invention, the apparatus comprises a support member and at least three radially adjustable contacting members coupled to the support member, wherein each of the at least three radially adjustable contacting members comprises a surface for contacting with the human head and at least one of the radially adjustable contacting members comprises a sensor for sensing the position of the at least one radially adjustable contacting member relative to the support member. In a further embodiment, the apparatus comprises at least four radially adjustable contacting members.

In another embodiment of the invention, the apparatus comprises a support member, at least three radially adjustable contacting members coupled to the support member and at least one sensor for sensing the position of at least one of the at least three radially adjustable contacting members relative to the support member, wherein each of the at least three radially adjustable contacting members comprises a surface for contacting with the human head.

In another embodiment of the invention, the apparatus comprises a support member, a plurality of radially adjustable contacting members coupled to the support member and a wireless transmitter, wherein each of the plurality of radially adjustable contacting members comprises a surface for contacting with the human head and least one of the radially adjustable contacting members comprises a sensor for sensing the position of the at least one of the radially adjustable contacting members relative to the support member.

In another embodiment of the invention, the apparatus comprises a support member, a plurality of radially adjustable contacting members coupled to the support member, a wireless transmitter and at least one sensor for sensing the position of at least one of the plurality of radially adjustable contacting members relative to the support member, wherein each of the plurality of radially adjustable contacting members comprises a surface for contacting with the human head.

The invention also encompasses methods of determining the outer contour of a human head and of detecting the presence or absence of cranial abnormality and/or disease.

In centering the device on the subject's head, at least two contacting members can be individually adjusted to give the same measurement or the two contacting members can be connected to each other so that an adjustment to one causes and adjustment to the at least one other connected contacting member.

One embodiment of the invention comprises positioning about the human head a plurality of contacting members rotatably coupled to a support member; adjusting each of the contacting members such that a curved surface of the contacting member having a radius of curvature that one of increases and decreases in a direction of rotation touches a surface of the human head; and/or measuring the contour of the human head after the plurality of contacting members have been adjusted to contact the human head.

Another embodiment of the invention comprises positioning about the human head a plurality of adjustable contacting members that are coupled to a support member; adjusting each of the adjustable contacting members such that a surface of the adjustable contacting member touches a surface of the human head, wherein at least two of the adjustable contacting members are connected to each other so that an adjustment to one of the connected adjustable contacting members causes a proportional adjustment to the at least one other connected adjustable contacting member; locking at least one of the adjustable contacting members; and/or measuring the contour of the human head after the plurality of adjustable contacting members have been adjusted to contact the human head.

Another embodiment of the invention comprises positioning about the human head a plurality of radially adjustable contacting members that are coupled to a support member; adjusting each of the radially adjustable contacting members such that a surface of the radially adjustable contacting member moves radially to touch a surface of the human head, wherein at least two of the radially adjustable contacting members are connected to each other so that an adjustment to one of the connected adjustable contacting members causes a proportional adjustment to the at least one other connected adjustable contacting member; and/or measuring the contour of the human head after the plurality of radially adjustable contacting members have been adjusted to contact the human head.

Another embodiment of the invention comprises positioning about the human head a plurality of contacting members that are coupled to a support member; adjusting each of the adjustable contacting members such that a surface of the contacting member touches a surface of the human head; and/or measuring the contour of the human head using indicia on at least one of the adjustable contacting members after the plurality of adjustable contacting members have been adjusted to contact the human head.

A further embodiment of the invention comprises the steps of positioning about the human head a plurality of contacting members that are coupled to a support member; adjusting each of the adjustable contacting members such that a surface of the contacting member touches a surface of the human head; and/or measuring the contour of the human head using indicia on the support member after the plurality of adjustable contacting members have been adjusted to contact the human head.

Another embodiment of the invention comprises positioning about the human head at least three radially adjustable contacting members that are coupled to a support member;

adjusting each of the radially adjustable contacting members such that a surface of the radially adjustable contacting member touches a surface of the human head; electronically transmitting a measurement from at least one of the radially adjustable contacting members to a device; and/or measuring the contour of the human head after the at least three radially adjustable contacting members have been adjusted to contact the human head.

Another embodiment of the invention comprises positioning about the human head a plurality of adjustable contacting members that are coupled to a support member; adjusting each of the adjustable contacting members such that a surface of the contacting member touches a surface of the human head; wirelessly transmitting a measurement from at least one of the adjustable contacting members to a device; and/or measuring the contour of the human head after the plurality of adjustable contacting members have been adjusted to contact the human head.

Another embodiment of the invention comprises positioning about the human head a plurality of adjustable contacting members that are coupled to a support member; adjusting each of the adjustable contacting members such that a surface of the adjustable contacting member touches a surface of the human head; measuring the contour of the human head after the plurality of adjustable contacting members have been adjusted to contact the human head; and/or based on the measurements, detecting the cranial abnormality in the human head.

3. FIGURES

FIG. 1. is a depiction of an embodiment of the apparatus. Spiral contacting members 1 are arrayed around the support member 2 and are rotabaly mounted to the support member at coupling or pivot points 3. Each coupling point 3 also comprises a pointer 4. The anterior and posterior contacting members 4 are connected to each other via a yoke 5. The yoke in this embodiment is pivotally attached to each anterior and posterior contacting member at a pivot points 6. The spiral contacting members each comprise a contacting surface 7 for contacting with a subject's head. The contacting members also have indicia 8 thereon which can indicate a degree or length measurement.

4. DETAILED DESCRIPTION

The invention allows rapid collection of multiple measurements on a subject's head in a non-invasive way. The apparatus and methods disclosed herein can be easily used by primary care pediatricians and other clinicians, and also by parents who wish to follow suspected cranial abnormalities in their children or simply to assess the degree of flattening in positional plagiocephaly.

Figure 2:
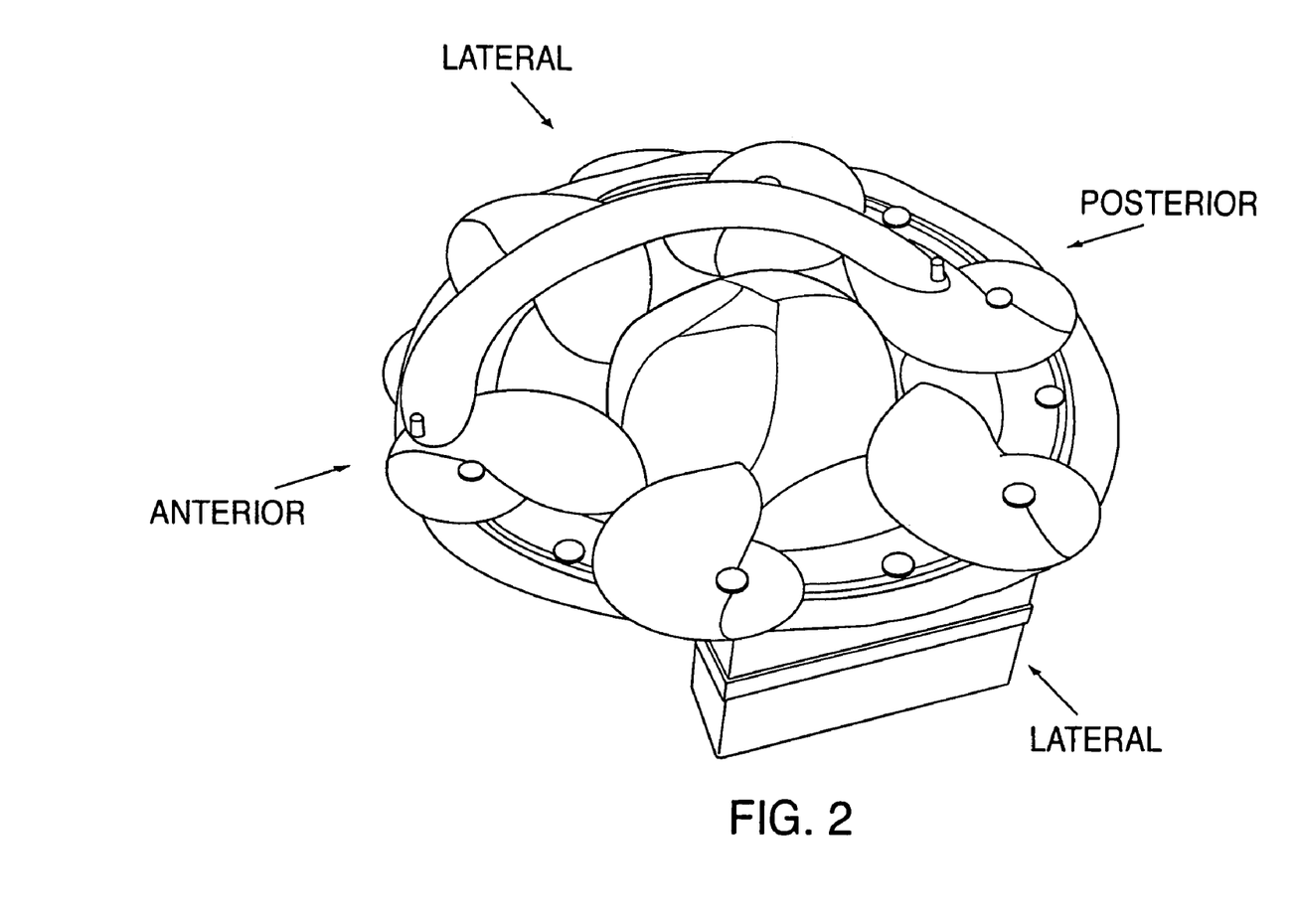
FIG. 2. depicts an apparatus placed in the transverse plane of a subject's head just above the orbital sockets and external auditory meati. This depiction shows the AP (anterior-posterior) and lateral dimensions of a subject's head.

One aspect of the invention comprises an apparatus consisting of a support member that is capable of being positioned about a subject's head, the support member having mounted to it a plurality of contacting members that can come into contact with the subject's head. The apparatus is placed in the transverse plane above the subject's orbital sockets and ears. See FIG. 2.

The contacting members may be adjustable so that they can be brought into and out of contact with the subject's head. Alternatively, the contacting members can be fixed. Thus, the invention encompasses an apparatus comprising a plurality of fixed and/or adjustable contacting members. Once the contacting member contacts the subject's head, a measurement can be made based on the position of the contacting member. From these measurements, a representation of the outer contour of the subject's head can be derived, which can then be used for diagnosis or sequential monitoring.

As more contacting members are mounted on the apparatus, more data points can be derived, and a more detailed representation of the outer contour of the subject's head can be made. The contacting members provide the clinician with data that can be used to calculate the shape of the outer contour of the subject's head. The data provided by the contacting members can be linear distance measurements provided in units such as millimeters, centimeters, decimeters, meters and inches, and/or angular measurements provided in such units as radians and degrees.

The apparatus also provides a mechanism for centering the apparatus on a subject's head once the support member has been placed about the subject's head. Centering the device about a subject's head standardizes the measurements thereby facilitating comparison to earlier or later measurements. In one aspect of the invention, the apparatus is centered in the anterior-posterior (AP) direction of the transverse or horizontal plane of the subject's head. In another aspect of the invention, the apparatus is centered in the lateral direction of the transverse or horizontal plane of the subject's head. See FIG. 2. The apparatus is centered in each of these directions by insuring that at least two contacting members, for example a contacting member making contact at the anterior portion of the subject's head and a contacting member making contact at the posterior portion of the patient's head, both provide measurements in a fixed ratio. In one embodiment of the invention a pair of contacting members being used to center the device provide identical measurements. Mechanisms for centering the apparatus are described in detail in section 4.2.1, below.

Another aspect of the invention provides methods of measuring the outer contour of a subject's head and diagnosing and/or detecting the presence of a cranial abnormality or disease. These methods are described in more detail in section 5, below. Section 6, below, describes how to interpret the data collected using the apparatus and methods of the invention. Examples of diseases and abnormalities that are diagnosable and/or detectable using the invention are described in more detail in section 7, below.

4.1 Support Member

The support member is a location for mounting a plurality of contacting members. The invention contemplates a support member suitable for mounting about a human head. The shape of the support member can be any shape known in the art, including but not limited to a circle, and ellipse or a rectangle. In certain embodiments of the invention where the apparatus comprises an elliptical support member or a support member that substantially conforms to the elliptical outer contour of a human head, the apparatus is oriented about the subject's head so that the support member substantially matches the elliptical contour of a human head when viewed in the horizontal or transverse plane. Thus, such support members will have anterior and posterior portions corresponding to the anterior and posterior portions of the subject's head and two lateral portions of the support member corresponding the lateral portions of the subject's head.

The cross-sectional shape of the support member can be any shape known in the art, including but not limited to a circle, an oval, an ellipse, a square or a rectangle. Furthermore, the support member can be hollow or completely solid. The support member can be also be very thin, e.g., less than a millimeter in thickness. The support member can be constructed of various materials described in detail in section 4.8, below.

In various embodiments, the support member is sized to accommodate the general head size of the particular population to be measured. As specified above in section 4.2 below, in one embodiment, the contacting members can have a removable portion so that larger heads can be accommodated. In another embodiment of the invention, the support member is adjustable so that it can accommodate various head sizes. This can be accomplished by using links which are added to the support member to increase the circumference of the support member, or by a sliding mechanism wherein the support member is expanded by sliding apart two portions of the support member. Such a sliding mechanism can optionally have a lock to lock the mechanism in position thereby maintaining the support member in an expanded configuration. For example, in one embodiment, a thumbscrew can be used to lock the sliding mechanism in position. The support member can have a plurality of such sliding mechanisms.

The support member can also house a power source such as batteries, various electrical equipment such as sensors and transmitters, electronic readouts and locking mechanisms. These are described in sections 4.3-4.7 below. The support member can also comprise gears or pulleys, for example, so that a single adjustment can adjust two or more contacting members. These mechanisms are described in more detail in section 4.2.1 below.

4.2 Contacting Members

One aspect of the invention comprises an apparatus comprising a support member having mounted to it a plurality of contacting members that can come into contact with the subject's head. The contacting members are either adjustable, so that they can be brought into and out of contact with the subject's head while keeping the support member stationary, or fixed. The apparatus can comprise a plurality of both fixed and adjustable contacting members. Once the contacting member contacts the subject's head, a measurement can be made based on the position of the contacting member. The distance measured can be between the subject's head and a point on the support member.

In one embodiment, the contacting members are linear rulers which can be adjusted to contact the subject's head. The contacting members can have indicia thereon for determining the distance between the support member and the subject's head. Alternatively, the support member can be marked with indicia in order to determine the distance between the support member and the subject's head. The rulers can be any suitable shape, including by way of example and not limitation, cylindrical, conical and rectangular or any combination thereof. In a specific embodiment, the rulers are be threaded like a screw so that they can be adjusted by axial rotation. The rulers can be adjusted radially inwards and outwards to and from the central area of the plane defined by the support member. Any mechanism known in the art can be used for adjusting the rulers, including but not limited to sliding or screwing the rulers.

In another embodiment, the contacting members are shaped as spirals and are rotabaly mounted on the support member so that they rotate to come in contact with the subject's head, and when the rotation is such that the spiral contacting member touches the surface of the subject's head, the angle of rotation of the spiral contacting member can be used to determine the radius formed by the spiral contacting member and the subject's head.

As a spiral contacting member is rotated, the radius of curvature of the contacting member's contacting surface either increases or decreases in the direction of rotation. Thus, knowing the equation that represents the radius of curvature of the contacting surface of the spiral contacting member and the angle of rotation of the contacting member, one can determine the radius from the pivoting point of the spiral contacting member to the subject's head and the tangent line at the contact point of the spiral contacting member and the subject's head.

For example, if a logarithmic spiral is used in the apparatus, the outer contour of the spiral can be represented by the polar coordinate equation:

$$r=ae^{b\theta}$$

r is the distance from the origin, $\theta$ is the angle from the x-axis, and a and b are arbitrary constants. Thus, if the angle or rotation of the spiral contacting member is known, the radius (distance to the head) can be easily computed. The origin would be represented by the pivot point of the spiral contacting member.

The angle of rotation of the contacting member can be determined using indicia either on the contacting member or the support member. When the indicia are present on the support member, the contacting member can have a window for viewing the angle of rotation measurement. Indicia can also be viewed using any of the display technologies disclosed herein such as in section 4.4 below, or known to one skilled in the art.

The essential feature of each spiral contacting member is that different points along its contacting surface will represent a different radius and a different tangent line. Any spiral shape defined by any spiral equation is suitable for use in the invention. By way of example and not limitation, a linear spiral and a logarithmic spiral are suitable spiral shapes for use in the invention.

There is inherently a small unusable part of the spiral and it is also desirable to have rounded edges to minimize the risk of skin irritation from a sharp point. In one embodiment of the invention, the unusable part of the spiral is a smooth polynomial with smooth first derivative.

The spiral contacting members can be mounted to pivot in the same plane as that created by the support member, or can alternatively be mounted to rotate perpendicular to the plane created by the support member. See FIG. 2.

In one embodiment, the spiral contacting members have a removable portion so that the apparatus can be used on subjects with different head sizes. In one embodiment, the removable portion of the spiral contacting member is able to be reattached. This aspect of the invention is particularly useful in following a single individual where the device will not have to be used again for a smaller head. Thus, as the subject's head grows, the removable portions of the spiral contacting members can be removed to accommodate the increased head size. In one embodiment, the removable portion of the contacting member can be created by perforating the contacting member along the inner edge of the removable portion and can then be torn away when needed.

By arraying a plurality of contacting members around a support member, a numerical representation of the outer contour of the head can be made, which can be used to create a graphical representation. The more spiral contacting members that are arrayed around the support member, the more detailed a representation of the outer contour of the skull can be achieved. Either the numerical or graphical representation of the outer contour of the head can be used for diagnosis and sequential follow-up purposes.

Figure 3:
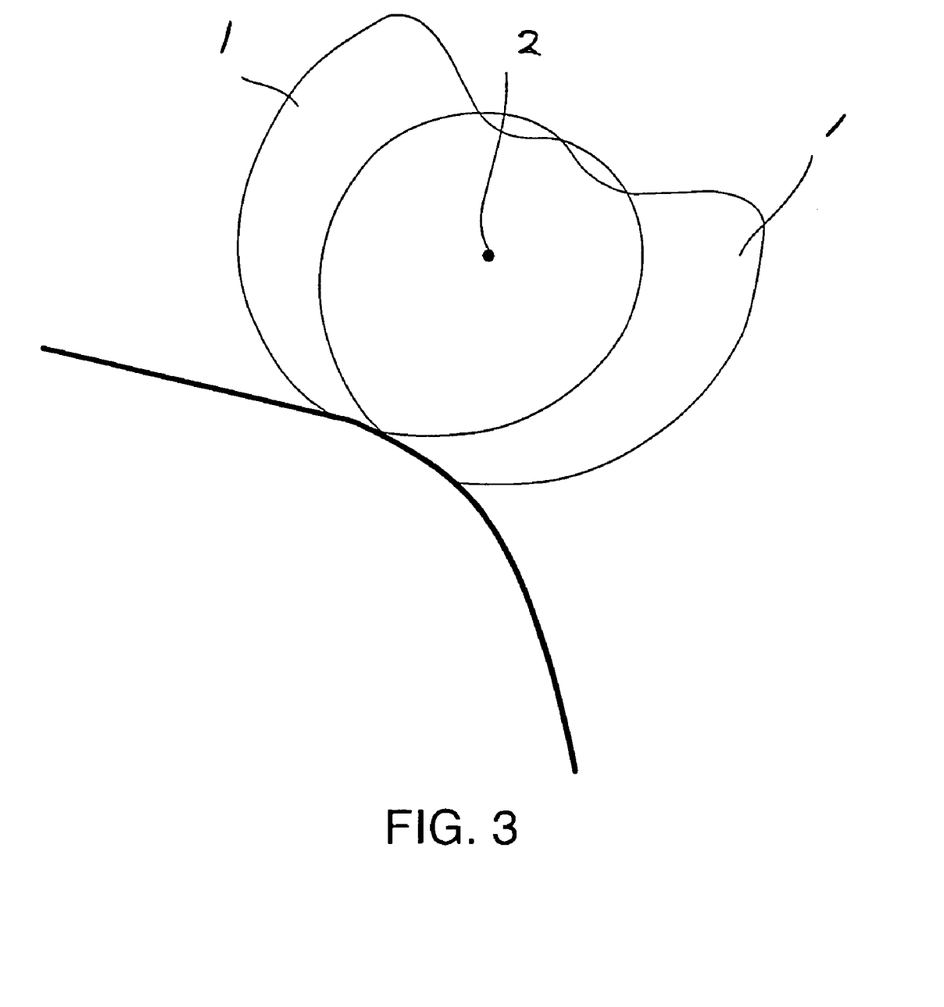
FIG. 3. depicts two overlapping spiral contacting members 1 that are mounted at the same pivot point 2 with both contacting members making contact at a different point along a curve.

The invention also provides an apparatus in which two or more spiral contacting members are mounted to the support member at the same pivot and/or coupling point, thereby having the same pivot and/or coupling point on the support member. The spiral contacting members sharing a pivot point can be mounted in opposite orientations, which would yield additional information when measuring an irregular curve, i.e., a curve with a non-uniform radius of curvature. See FIG. 3.

In one embodiment, the contacting members are coupled to the support member using magnets, an electromagnet and/or magnetic and/or electromagnetic force. The contacting members can further be coupled to the support member using adhesive, bolts, pins, clamps, springs, staples, screws or nails. Furthermore, the any non-moving portion of the contacting members can be integrated in to the support member, i.e., the stationary portion of the contacting members can be part of the support member. The contacting members can also be coupled to the support member through friction force.

4.2.1 Yoke

In order to standardize the measurements obtained by the invention, the invention contemplates connecting at least two of the contacting members together in such a way that an adjustment to one of the connected contacting members causes an adjustment to any contacting member connected to it. In another embodiment, the apparatus comprises at least two pairs of connected contacting members.

Figure 1:
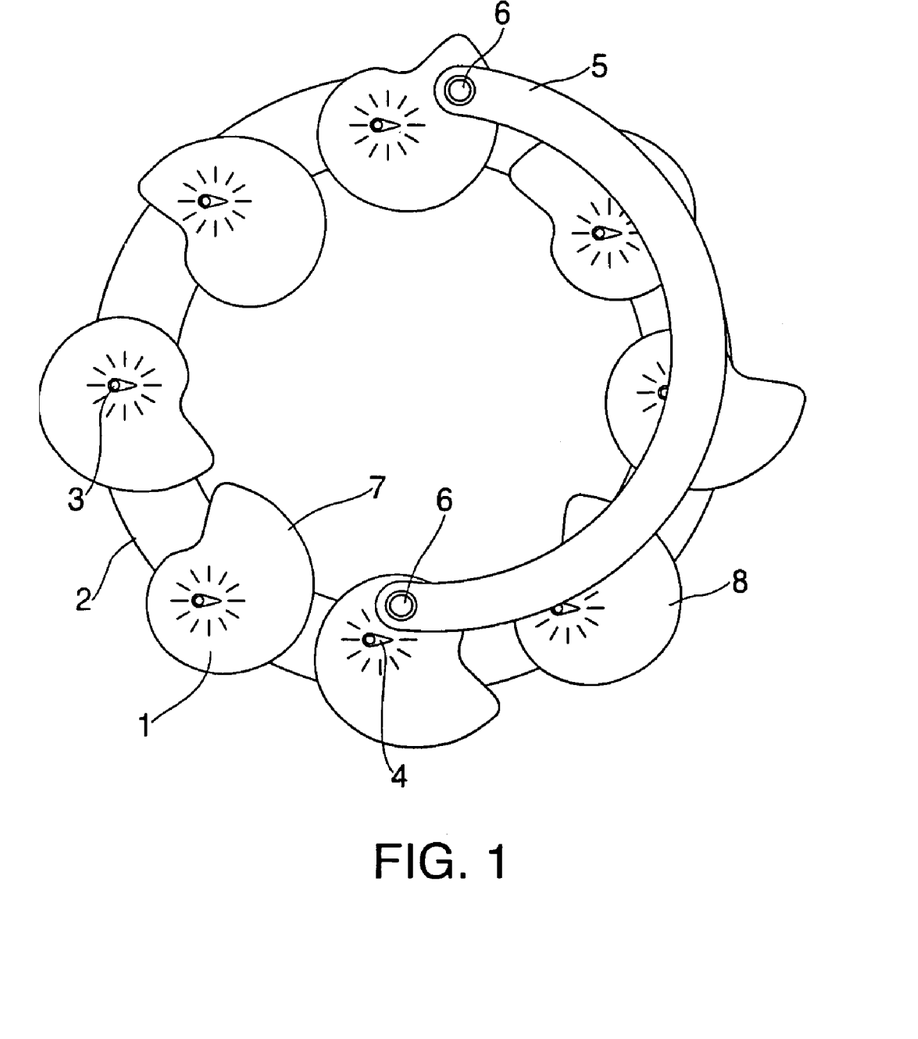

In one embodiment of the invention, at least two adjustable contacting members are connected so that an adjustment to one of the connected contacting members causes a proportional adjustment to the at least one other adjustable contacting member. In other words, a single adjustment adjusts the two connected contacting members. In another embodiment, adjusting one of the connected contacting members causes an equal adjustment in the at least one other connected contacting member. For example, if one linear ruler contacting member is radially adjusted 5 cm's toward the center of the area defined by the support member, the other connected linear ruler contacting member is also radially adjusted 5 cm toward the center of the area defined by the support member.

Where the contacting member are spirals, contacting members can be connected with a yoke. Any type of yoke known in the art can be used in the invention. The yoke can be in the same plane as the support member, or the yoke can leave the plane of the support member by arching over the top of the head. See FIG. 1. If spiral contacting members are being used, the connected contacting members are connected so that the same angle of rotation measurement is present with each connected contacting member. In embodiments of the invention, one yoke can be used for the AP spiral contacting members and a second yoke for the lateral spiral containing members.

In general, the contacting members other than the AP and lateral contacting members are not connected to each other because there may be different measurements for each of these spiral contacting members. However, the invention encompasses apparatus in which contacting members in addition to, or other than, the AP and lateral contacting members are connected to each other. The invention also encompasses apparatus in which more than two contacting members are connected to each other, e.g., three contacting members that are connected to each other so that an adjustment to one causes an adjustment to the other two connected contacting members.

The connected contacting members can be connected by any mechanism known in the art, so that an adjustment to one of the connected contacting members causes an adjustment to another connected contacting member connected to it, for example but not limited to gears, levers, pulleys and springs. In one embodiment of the invention, an adjustment to one connected contacting member causes a proportional adjustment in the other contacting members connected to it. In another embodiment of the invention, the connected contacting members adjust in unison. In yet another embodiment of the invention, the connected contacting members can be adjusted simultaneously using a single controller, including but not limited to a knob, lever, crank or switch. The connected contacting members can also be connected electronically, whereby a sensor which senses the position of the first connected contacting member electronically transmits the position of the contacting member to the at least one other connected contacting member. The connected contacting members can further comprise a motor which moves the contacting member, so that once the position of the first connected contacting member is received by the other connected contacting members, motors can adjust the connected contacting members.

4.3 Locking Mechanisms:

In order to facilitate the gathering of data provided by the invention, in one embodiment of the invention, the apparatus comprises a locking mechanism. In another embodiment, the apparatus comprises a plurality of locking mechanisms.

The locking mechanism can be used to lock a contacting member in place once the apparatus has been positioned on the human head. Such a locking mechanism facilitates removal of the apparatus without inadvertently moving the contacting members. Once removed, data from the contacting members can be analyzed. In one embodiment of the invention, a locking mechanism locks all of the contacting members. In another embodiment, each contacting member locks independently.

Any locking mechanism known to one skilled in the art can be used in the invention, including but not limited to a magnet, an electromagnet, a ratchet, a clamp, a screw, a pin, a bolt and a spring. The locking mechanism can also comprise a release mechanism whereby the locking mechanism is disengaged, allowing the contacting member to move again.

The locking mechanism can also, at least in part, be separate from the apparatus. For example, a clamp that is separate from the apparatus could be attached to the support member to cover the contacting members, thereby locking the contacting members in place.

4.4 Sensors

In order to facilitate gathering data from the contacting members, the invention encompasses an apparatus comprising one or more sensors. Any sensor known in the art can be used in the invention. Specifically, a sensor used in the invention senses the position of a contacting member. In one embodiment of the invention, the sensor senses the position of the contacting member in relation to the support member, another contacting member, a portion of the contacting member comprising the sensor and/or a fixed point separate from the apparatus.

The sensor can also be electronically linked to a digital or analog display that displays measurement data, such as linear distance and/or degrees. Any display technology known in the art could be used in the invention, including but not limited to liquid crystal displays and light emitting diode displays. In one embodiment, the apparatus comprises a plurality of such digital or analog displays. In a certain embodiment, the support member comprises such a display or displays. In another embodiment, a contacting member comprises such a display.

The sensors used in the invention can also be linked to each other electronically, either through wire or by using a wireless transmitter so that they can transmit data to each other. The sensors can be linked to a device, for example a computer, calculator or a portable electronic device, either through a wire or by using a wireless transmitter so that the sensors can transmit data to such devices.

In one embodiment of the invention, the apparatus comprises at least one sensor. In another embodiment of the invention the apparatus comprises a plurality of sensors. In yet another embodiment of the invention, the support member of the apparatus comprises a sensor. In another embodiment, at least one of the contacting members comprises a sensor. In yet another embodiment, a plurality of contacting members comprise a sensor.

4.5 Wireless Transmission

One aspect of the invention encompasses wirelessly transmitting measurements made by contacting members of the apparatus to a device such as a computer, calculator or portable electronic device. By way of example and not limitation, sensors contained in the apparatus can wirelessly transmit data to a device. The sensors can also transmit their data, by wire, to a wireless transmitter which then transmits the data wirelessly to a device. In one embodiment of the invention the device is an electronic device, e.g., a computer and/or a calculator.

After the data has been wirelessly transmitted from the apparatus to the device, the device computes the shape of the outer contour of the subject's head using a software program. The device can also provide a diagnosis based on the data transmitted to it and/or detect the presence or absence of a cranial disease and/or abnormality. The device can be set up to follow the progression of a cranial disease and or abnormality over time by comparing measurements taken at one point in time with measurements taken before or after that point in time. By comparing earlier and later measurements, the device can also determine if the subject's head is developing normally or abnormally.

In one embodiment, the device graphically displays the shape of the outer contour of the subjects head on a display, including but not limited to a cathode ray tube or a liquid crystal display. The device can also allow manipulation of the image using any technology known in the art such as software programs. For example, the image can be enlarged or reduced in size, rotated and inverted. A graphical representation can be printed out with any printing technology known in the art.

In one embodiment, the device also comprises a database or alternatively can be electronically connected to a database. The database can comprise data of normal and/or abnormal heads to be used for comparison purposes, and or data about a particular subject's head for comparison purposes.

In one embodiment of the invention, the apparatus comprises at least one wireless transmitter or a plurality of wireless transmitters. Any wireless transmitter known in the art can be used in the invention. A wireless transmitter can either be housed in the support member or in at least one contacting member.

4.6 Readout

A method of reporting the position of spiral contacting members most simply could be printed numbers and/or indicia around the perimeter with a pointer indicating the number amount of rotation of the contacting member. The pointer can be attached to the pivot, or it can be part of the pivot, so that it remains stationary while the spiral contacting member is rotated. Alternatively a window could be made in the spiral so that the number would be read on the ring. Alternatively, the pointer and/or numbers and/or indicia also be placed on the support member. An electronic display, such as one described in section 4.4, above, can be used to indicate the amount of rotation of each spiral contacting member.

For each linear ruler contacting member, the pointer and/or numbers and/or indicia can be placed either on the support member, the contacting members, or both. A window can also be used, either on the support member or on the contacting member, to read the number. An electronic display, such as one described in section 4.4, above, can be used to indicate the amount of rotation of each linear ruler contacting member.

4.7 Power Source

An apparatus that comprises electronic components, e.g., electronic displays, sensors and motors, can be powered by any source known in the art including batteries and/or AC or DC electricity. The batteries can be mounted directly in the apparatus, either in the support member or a contacting member.

4.8 Materials

The apparatus comprising the support member and contacting members can be constructed of any suitable material, by way of example and not limitation, foam, metal, metal alloys, plastic, paper, rubber or cardboard, or any combination thereof and can be translucent or opaque.

4.9 Contacting Members for Contacting the Ear Including the External Auditory Meatus Deformational plagiocephaly deforms the whole skull in a parallelogram fashion, so the ear on the side flattened in the back is pushed forward relative to the other ear (often by 10-20 mm, measured on the AP axis). In one embodiment of the invention, at least one contacting member is for contacting the ear, including and portion thereof such as the external auditory meatus. This embodiment of the apparatus measures the displacement of the ears in the AP direction. This type of measurement can both further quantify any asymmetry, and can make a diagnostic distinction. For, example, in positional plagiocephaly, the ear goes forward, but if the flattening is caused by fusion of the lambdoid suture (lambdoid synostosis, which is very rare but an important theoretical differential diagnosis, because it could imply a need for surgery in selected cases), the ear may be displaced in the posterior direction.

Figure 4:
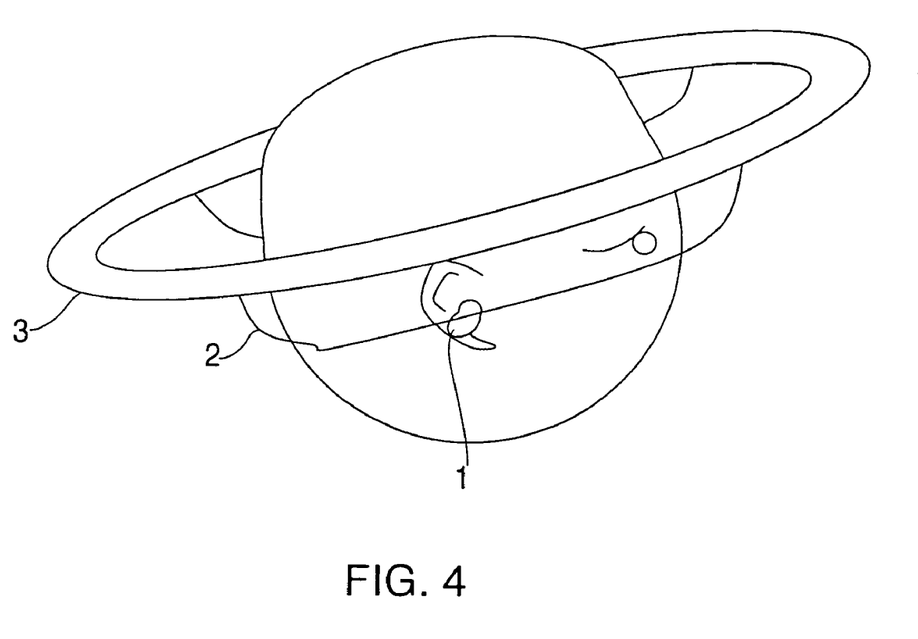
FIG. 4. depicts a contacting member that is for contacting an external auditory meatus of the subject, comprising an earpiece 1 and a secondary support member 2 attached to a support member 3.
Figure 5A:
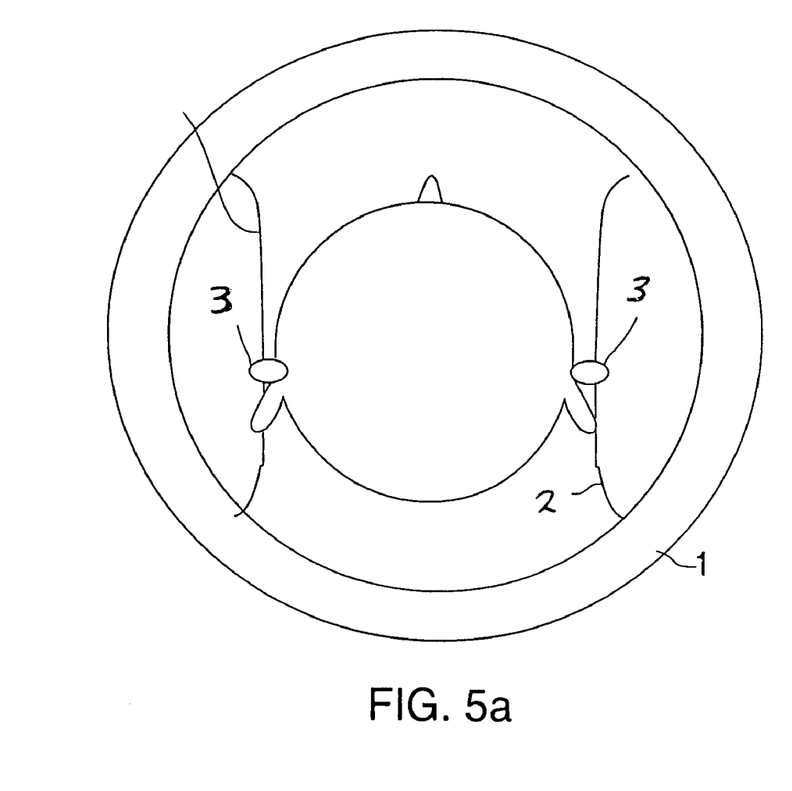
FIG. 5a. depicts an overhead view of an apparatus positioned on a subject's head showing the support member 1, secondary support member 2 and earpieces 3. The figure depicts equal AP distances of the external auditory meati typical in a normal head.
Figure 5B:
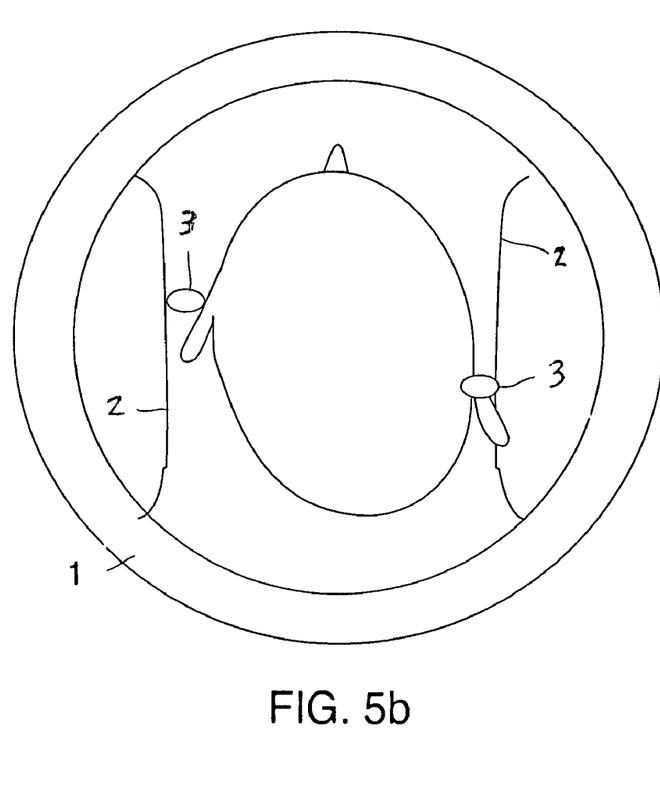
FIG. 5b. depicts an overhead view of an apparatus positioned on a subject's head showing the support member 1, secondary support member 2 and earpieces 3. The figure depicts different AP distances of the external auditory meati typical in plagiocephaly.
Figure 6A:
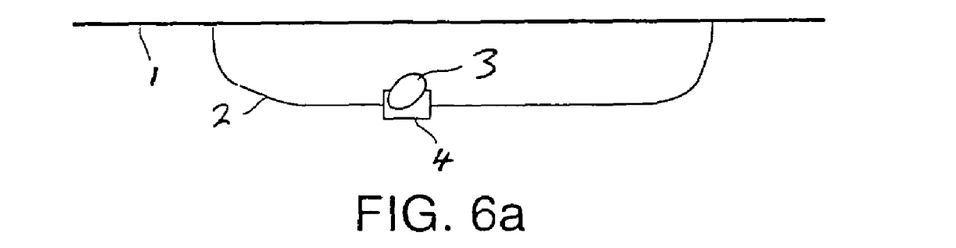
FIG. 6a. depicts a lateral view of a support member 1, a secondary support member 2, and a contacting member for contacting with the external auditory meatus comprising an earpiece 3 and slider 4.
Figure 6B:
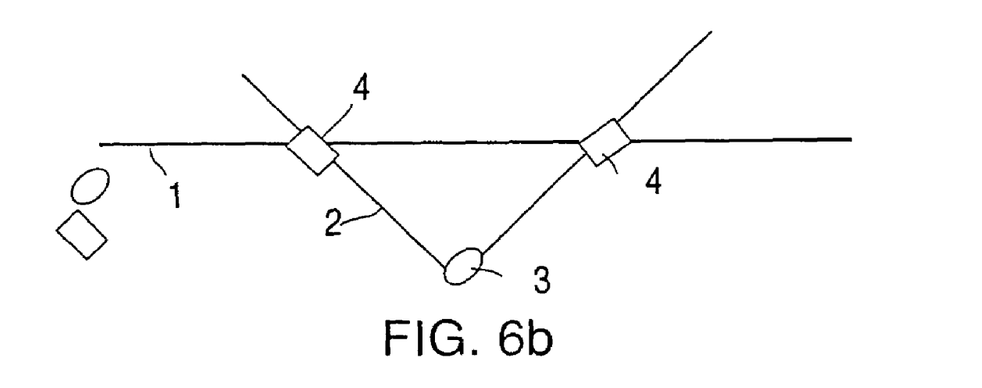
FIG. 6b. depicts a lateral view of a support member 1, a secondary support member 2, and a contacting member for contacting with the external auditory meatus comprising an earpiece 3. Sliders 4 are fixed to the support member.
Figure 6C:
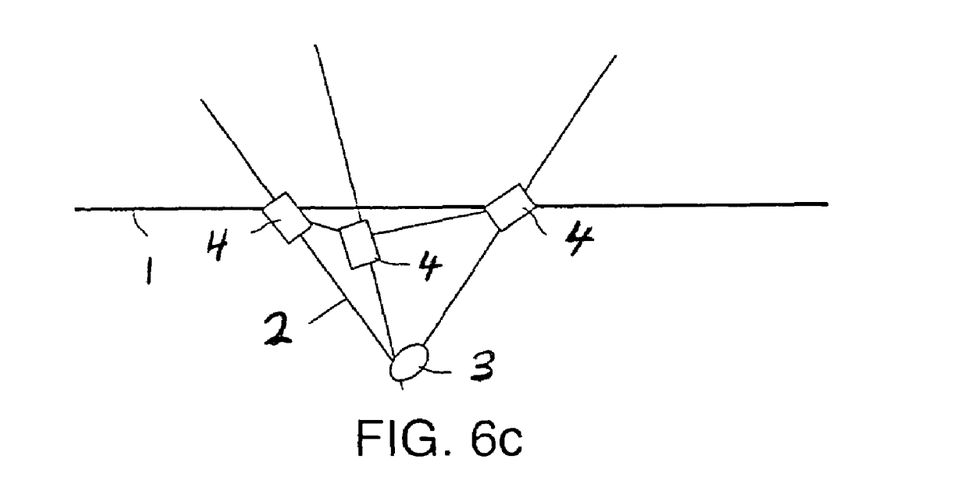
FIG. 6c. depicts a lateral view of a support member 1, a secondary support member 2, and a contacting member for contacting with the external auditory meatus comprising an earpiece 3. Sliders 4 are fixed to the support member.

For illustrative purposes, FIG. 4 shows the contacting members for contacting the ears, but not the contacting members for contacting with the skull. The contacting member in this embodiment is comprised of an earpiece and optionally a slider used to determine length and to facilitate moving the earpiece along the secondary support member. The earpiece and/or slider may slide along a secondary support member. Such a secondary support member can be marked with indicia to indicate length. In one embodiment, the contacting member comprises an earpiece for example, an earplug, earbud headphone piece or stethoscope earpiece) which is able to slide along the frame of the secondary support member so that it can be positioned in and/or on the subject's external auditory meatus or other suitable landmark on the subject's ear. In a further embodiment, the earpiece can be localized using a secondary support member with 1, 2 or 3 degrees of freedom, which can give AP distance; AP and vertical distance; or AP, vertical and lateral distance, respectively. See FIGS. 6a, 6b and 6c, respectively. In this embodiment, when more than one degree of freedom is desired, the sliders are fixed to the main support member and instead the secondary support member slides within the sliders allowing positioning of the earpiece. The secondary support member in this embodiment can also either be attached to the support member by a hinge or comprise a hinge so that the contacting member can be swung out of the way.

5. UTILIZATION

The invention provides methods of determining the outer contour of a subject's head. In one embodiment of the invention, the apparatus is positioned in the transverse or horizontal plane of the subject's head. In another embodiment of the invention, the apparatus positioned in the plane of the largest anterior-posterior (AP) and lateral diameters of the subject's head, which allows for standardization of measurements between patients.

The following example of a method for determining the outer contour of a subject's head is given by was of example and not limitation:

The apparatus is placed to be in the plane of the subject's head above the orbital rims and above the ears. The contacting members in the AP dimension are set first. The AP contacting members can be comprised of as few as a single pair of contacting members (one contacting member in the anterior portion of the apparatus and one contacting member in the posterior portion of the apparatus). In order to center the head in the AP direction, the AP contacting members are either individually manually turned so that they are equivalently adjusted (i.e., they are identically spaced from the support member to the head) or the contacting members are connected such that a single adjustment ensures that they are equivalently adjusted. The AP contacting members are adjusted so that they just come into contact with the subject's head. Next, the lateral contacting members are similarly adjusted to center the head in the lateral direction. Each of the other contacting members are then adjusted to just contact the contacting member with the subject's head. Once all of the contacting members arrayed on the support member are adjusted to contact the subject's head, the contacting members can optionally be locked in place. At this point, the entire ring is removed from the subject's head and the results are recorded. They can be either written down or recorded electronically via sensors and a connection (either wired or wirelessly) to a computer, calculator or portable electronic device. The results can then be graphed to create representation of the outer contour of a subject's head.

6. INTERPRETING THE DATA

The apparatus disclosed herein provides data from each contacting member. If the contacting member is a linear ruler, the data provided will be linear distance from a reference point on the support member to the subject's head. If the contacting member is a spiral contacting member, these data can be a linear distance and/or an angular measurement such as degrees or radians.

For example, once contacted with the human head, spiral contacting members can provide an angular measurement. Once the angular measurement is determined, the radius from the pivot point of the contacting member to the head and the tangent line at the contact point can calculated using the equation representing the curved contacting surface of the spiral contacting member.

Once the dimensions of the subject's head are determined with the device, the results can be graphed on appropriately ruled graph paper, for example, customized polar coordinate form or Cartesian form. Alternatively, the data provided by the invention can be entered into a calculator or computer that can graph and/or interpret the data. The data can also be transmitted to a calculator, computer or portable electronic device through a wire or wirelessly, as described in section 4.5, above.

The simplest way to graph the data, after positioning the apparatus, adjusting the contacting members to make contact with the subject's head and removing the apparatus without moving the contacting members, is to lay the apparatus over paper and mark the point of contact between the subject's head and each of the contacting members. Then each marked point can be connected yielding a graphical representation of the outer contour of the subject's head. If spiral contacting members are being used, the tangent lines can be drawn at each contact point. A tangent line can be extended until it intersects the tangent lines created by the adjacent spiral contacting members to create a representation of the outer contour of the head. Alternatively, the tangent points can be connected to create a representation of the outer contour of the head.

The data can also be entered into a computer, calculator or portable electronic device, so that the computer or calculator can aid in graphing and interpreting the data. The computer, calculator or other electronic device including portable electronic devices, can calculate the linear distance based on the angular measurement, or the linear measurement can be entered directly. A program used for graphing and interpretation can base any graphs and/or interpretation on the dimensions of the support member, the position of each contacting member on the support member and the linear distance from the support member to the subject's head.

Once the linear distance between each contacting member and the subjects head is known, a clinician or parent for example can interpret the data and detect the presence or absence of a cranial disease or abnormality. For example, assuming there are twelve contacting members, with each contacting member assigned a sequential number from one to 12 similar to a clock face, the diameter of the subject's head based on the contacting members at position 2 and 8 can be compared to the diameter of the subject's head based on the contacting members at positions 10 and 4. If the diameters are unequal by more than a threshold percentage, an abnormal diagnosis can be made. Positional plagiocephaly might produce such a result, for example.

Another measurement that can be useful in diagnosis is the ratio of the lateral diameter to the AP diameter. Normally this ratio is greater than 0.75. If the number is less than 0.75, it might suggest the presence of sagittal synostosis, for example. Some cranial diseases and abnormalities that are detectable using the invention are listed in section 7, below.

Once a cranial abnormality is detected an appropriate treatment can be formulated, such as an orthotic device or surgery.

7. DISEASES OF THE CRANIUM

The invention disclosed herein in all of its embodiments can be used to diagnose and/or follow a host of cranial diseases and/or abnormalities, including but not limited to cranial asymmetry, craniofacial asymmetry, benign positional molding, posterior plagiocephaly, occipital plagiocephaly, plagiocephaly without synostosis, deformational plagiocephaly, craniosynostosis, lambdoid craniosynostosis, sagittal craniosynostosis, coronal craniosynostosis, metopic craniosynostosis, squamosal craniosynostosis, syndromic synostosis and nonsyndromic craniosynostosis.

The invention disclosed herein in all of its embodiments can be used to establish a normal and/or disease-free status of a subject's head. Furthermore, the invention disclosed herein in all of its embodiments can be used to assess the efficacy of various treatment modalities, including but not limited to surgery, medication and/or the use of orthotic devices, including but not limited to head bands, in correcting the disease and/or abnormality.

The invention disclosed herein can also be used by parents or clinicians, for example, to track the development of the shape of an infant's skull over time.

8. SUBJECTS

The invention disclosed herein in all of its embodiments is directed to measuring and determining the shape of the outer contour of a subject's head. In one embodiment of the invention the subject is a mammal. In another embodiment the subject is a human. In yet another embodiment of the invention the subject is a child, infant and/or baby. In a specific embodiment of the invention, the subject is under 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 years of age. In another embodiment of the invention the subject is a patient. In yet another embodiment of the invention the subject has at least one of the cranial diseases and/or abnormalities disclosed in section 7, above.

The invention claimed is:

1. An apparatus for determining an outer contour of a human head, comprising a support member and a plurality of contacting members rotatably coupled to the support member wherein each of the plurality of contacting members comprises a curved surface for contacting with the human head and wherein the curved surface of each contacting member has a radius of curvature that is one of increasing and decreasing in a direction of rotation.

2. The apparatus of claim 1, wherein twelve contacting members are rotatably coupled to the support member.

3. The apparatus of claim 1, wherein the contacting members have indicia thereon.

4. The apparatus of claim 1, wherein at least two contacting members are rotatably coupled to the support member at one coupling point.

5. The apparatus of claims 1, wherein the curved surface of the contacting members comprises a portion which is characterizable by a spiral equation.

6. The apparatus of claim 5, wherein the spiral equation characterizes a linear spiral.

7. The apparatus of claim 5, wherein the spiral equation characterizes a logarithmic spiral.

8. The apparatus of claim 4, wherein the curved surface of the contacting member comprises a portion which is characterizable by a spiral equation.

9. The apparatus of claim 8, wherein the spiral equation characterizes a linear spiral.

10. The apparatus of claim 8, wherein the spiral equation characterizes a logarithmic spiral.

11. An apparatus for determining an outer contour of a human head, comprising a support member; a plurality of contacting members rotatably coupled to the support member wherein each of the contacting members rotatably coupled to the support member comprises a curved surface for contacting with the human head wherein the curved surface of each rotatably coupled contacting member has a radius of curvature that is one of increasing and decreasing in a direction of rotation; and at least one contacting member comprising a portion that conforms to an external auditory meatus of the human head.

12. The apparatus of claim 11, wherein twelve contacting members are rotatably coupled to the support member.

13. The apparatus of claim 11, wherein the contacting members have indicia thereon.

14. The apparatus of claim 11, wherein at least two contacting members are rotatably coupled to the support member at one coupling point.

15. The apparatus of claims 11, wherein the curved surface of the contacting member comprises a portion which is characterizable by a spiral equation.

16. The apparatus of claim 15, wherein the spiral equation characterizes a linear spiral.

17. The apparatus of claim 15, wherein the spiral equation characterizes a logarithmic spiral.

18. The apparatus of claims 14, wherein the curved surface of the contacting member comprises a portion which is characterizable by a spiral equation.

19. The apparatus of claim 18, wherein the spiral equation characterizes a linear spiral.

20. The apparatus of claim 18, wherein the spiral equation characterizes a logarithmic spiral.

* * * * *